(12) United States Patent
Sara

(10) Patent No.: US 10,278,757 B2
(45) Date of Patent: May 7, 2019

(54) TEMPERATURE AND STRAIN MEASUREMENT TECHNIQUE DURING CRYOABLATION

(71) Applicant: Medtronic CryoCath LP, Toronto (CA)

(72) Inventor: Rahmani Sara, Montreal (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 653 days.

(21) Appl. No.: 14/918,113

(22) Filed: Oct. 20, 2015

(65) Prior Publication Data
US 2017/0105780 A1  Apr. 20, 2017

(51) Int. Cl.
*A61B 5/00* (2006.01)
*A61B 5/01* (2006.01)
(Continued)

(52) U.S. Cl.
CPC .............. *A61B 18/02* (2013.01); *A61B 5/01* (2013.01); *A61B 5/4836* (2013.01); *A61B 18/1492* (2013.01); *A61B 2018/0022* (2013.01); *A61B 2018/00375* (2013.01); *A61B 2018/00577* (2013.01); *A61B 2018/00714* (2013.01);
(Continued)

(58) Field of Classification Search
CPC ............ A61B 18/02; A61B 2018/0212; A61B 2018/0262; A61B 2018/00005; A61B 2018/00214; A61B 2018/0022; A61B 2018/00636; A61B 2018/00642; A61B 2018/00696; A61B 2018/00714; A61B 2018/00791; A61B 2018/00797
See application file for complete search history.

(56) References Cited

U.S. PATENT DOCUMENTS 6,024,488 A  2/2000  Wu et al.
6,178,346 B1 1/2001 Amundson et al.
(Continued)

OTHER PUBLICATIONS

Song et al., "A simultaneous strain and temperature sensing module based on FBG-in-SMS", 2014, Measurement and Science Technology, vol. 25, No. 5.*
Nair et al., "Process Monitoring of Fibre Reinforced Composites using a Multi-Measurand Fibre-Optic Sensor", 2015, Sensors and Actuators B Chemical, 212.*
(Continued)

*Primary Examiner* — Ronald Hupczey, Jr.
(74) *Attorney, Agent, or Firm* — Christopher & Weisberg, P.A.

(57) ABSTRACT

A device, system, and method for identifying an area of ablated tissue and/or assessing contact between a treatment element and tissue and/or assessing occlusion of a body lumen by the treatment element. Specifically, the device, system, and method may include a device having one or more fiber sensors and a processing unit for receiving emitted and/or reflected light from tissue and making one or more determinations based on the received light regarding ablated tissue, tissue contact, and/or occlusion. Each of the fiber sensors may include at least one multimode waveguide segment and at least one singlemode waveguide segment, or each of the fiber sensors may be singlemode waveguide including fiber Bragg grating for assessing strain of a treatment element by tissue contact. The processing unit may include a beam processing apparatus and a hyperspectral imaging and analysis apparatus, and may optionally include a light source.

16 Claims, 12 Drawing Sheets

(51) Int. Cl.
*A61B 18/00* (2006.01)
*A61B 18/02* (2006.01)
*A61B 18/14* (2006.01)

(52) U.S. Cl.
CPC ............... *A61B 2018/00791* (2013.01); *A61B 2018/00821* (2013.01); *A61B 2018/0212* (2013.01); *A61B 2018/0262* (2013.01); *A61B 2562/0233* (2013.01); *A61B 2562/0238* (2013.01); *A61B 2562/0271* (2013.01)

(56) References Cited

U.S. PATENT DOCUMENTS

| | | | |
|---|---|---|---|
| 7,717,618 | B2 | 5/2010 | Saxena et al. |
| 8,406,859 | B2 * | 3/2013 | Zuzak ............... A61B 5/0071 257/440 |
| 2002/0147394 | A1 | 10/2002 | Ellingsen |
| 2004/0002749 | A1 * | 1/2004 | Joye ............... A61B 1/00082 607/105 |
| 2006/0122587 | A1 | 6/2006 | Sharareh |
| 2006/0229515 | A1 | 10/2006 | Sharareh et al. |
| 2007/0078450 | A1 | 4/2007 | Langer |
| 2007/0232871 | A1 | 10/2007 | Sinofsky et al. |
| 2009/0143774 | A1 | 6/2009 | Uzunbajakava et al. |
| 2012/0197245 | A1 | 8/2012 | Burnett et al. |
| 2013/0090563 | A1 | 4/2013 | Weber |
| 2015/0141847 | A1 | 5/2015 | 'Sarvazyan |

OTHER PUBLICATIONS

International Search Report and Written Opinion dated Dec. 29, 2016, for corresponding International Application No. PCT/CA2016/051205; International Filing Date: Oct. 18, 2016 consisting of 8 pages.

Rajinder P. Singh-Moon, Near-infrared spectroscopy integrated catheter for characterization of myocardial tissues: preliminary demonstrations to radiofrequency ablation therapy for atrial fibrillation, Biomedical Optics Express 2494, Jul. 1, 2015, vol. 6, No. 7, DOI:10.1364/BOE.6.002494.

Hiroshi Nakagawa, MD, PhD et al., Comparison of In Vivo Tissue Temperature Profile and Lesion Geometry for Radiofrequency Ablation With a Saline-Irrigated Electrode Versus Temperature Control in a Canine Thigh Muscle Preparation, Circulation. 1995; 91: 2264-2273 doi: 10.1161/01.CIR.91.8.2264.

Ahmed Hisham E. Morshed, D6. Bending Characteristics of Single Mode-Multimode-Single Mode Optical Fiber Structures, 31st National Radio Science Conference (NRSC2014), Apr. 28-30, 2014, Faculty of Engineering, Ain Shams University, Egypt.

M. Broussely et al., Application of IR thermography for quantitative temperature measurements in a Thermal-Vacuum Space Simulator, 9th International Conference on Quantitative InfraRed Thermography, Jul. 2-5, 2008, Krakow, Poland.

S.W. James et al., Simultaneous independent temperature and strain measurement using in-fibre Bragg grating sensors, Electronics Letters, Jun. 6, 1996, vol. 32 No. 12.

* cited by examiner

US 10,278,757 B2

TEMPERATURE AND STRAIN MEASUREMENT TECHNIQUE DURING CRYOABLATION

CROSS-REFERENCE TO RELATED APPLICATION n/a

STATEMENT REGARDING FEDERALLY SPONSORED RESEARCH OR DEVELOPMENT n/a

TECHNICAL FIELD

The present invention relates to a device, system, and method for identifying an area of ablated tissue. The present invention also relates to a device, system, and method for assessing contact between a treatment element and tissue and/or assessing occlusion of a body lumen by the treatment element. Specifically, the device, system, and method may include one or more fiber sensors and a processing unit for receiving emitted and/or reflected light from tissue and making one or more determinations based on the received light regarding ablated tissue, tissue contact, and/or occlusion.

BACKGROUND

A cardiac arrhythmia is a condition in which the heart's normal rhythm is disrupted. Certain types of cardiac arrhythmias, including ventricular tachycardia and atrial fibrillation, may be treated by ablation (for example, radiofrequency (RF) ablation, cryoablation, ultrasound ablation, laser ablation, microwave ablation, and the like), either endocardially or epicardially.

Procedures such as pulmonary vein isolation (PVI) and pulmonary vein antrum isolation (PVAI) are commonly used to treat atrial fibrillation. These procedures generally involve the use of a cryogenic device, such as a catheter, which is positioned at the ostium of a pulmonary vein (PV) such that any blood flow exiting the PV into the left atrium (LA) is completely blocked. Once in position, the cryogenic device may be activated for a sufficient duration to create a desired lesion within myocardial tissue at the PV-LA junction, such as a PV ostium or PV antrum. If a cryoballoon is used as the treatment element of the cryogenic device, the balloon is typically inflated using a fluid refrigerant, enabling an entire outer diameter of the balloon to create a circumferential lesion about the ostium and/or antrum of the PV to disrupt aberrant electrical signals exiting the PV. Additionally or alternatively, the cryoballoon may also be used to treat cardiac wall tissue (for example, left atrial wall tissue), in which case the cryoballoon is positioned in contact with the target tissue.

The success of this procedure depends largely on the quality of the lesion(s) created during the procedure, and it therefore would be beneficial to monitor the temperature of the tissue being treated, in part as an indication of lesion quality. There are several ways in which lesion formation may be assessed, either during or after an ablation procedure. In many known devices, the temperature within the cryoballoon is monitored and correlated with the temperature of the tissue being treated. For example, many devices include a thermocouple located within the cryoballoon, which may be located proximate an outlet of a fluid injection lumen. During cryotreatment, liquid refrigerant (such as nitrous oxide) is injected into the inner balloon via the injection lumen. As the refrigerant is injected into the cryoballoon, it expands into the vapor state and causes a temperature decrease. The refrigerant vapor, which has absorbed heat from the cryoballoon-tissue interface, is drawn out of the cryoballoon, back into the shaft of the device and into the console by the console vacuum pump. In a PV isolation procedure, this cooling effect may cause a circumferential lesion about the PV ostium. Although the thermocouple may be used to measure temperature of the dynamic phase transition of nitrous oxide within the cryoballoon due to the heat exchange, the thermocouple does not monitor temperature of the treated tissue.

Another system for temperature measurement is the fluoroptic temperature measurement system. Fluoroptic temperature measurement involves the use of a special thermosensitive phosphorescent sensor located at the end of an optical fiber bundle. An elimination light source (LED, xenon lamp, or the like) is used to generate a light that is conveyed through the optical fiber to the thermo-sensitive phosphorescent sensor. Therefore, the phosphorescent sensor emits light over a broad spectrum. The time required for the fluorescence to decay is dependent upon the sensor's temperature. The illumination source is turned off and the generated light from the excited fluorescent sensor is collected. For example, the emitted light from the fluorescent sensor is conveyed back to an optical detector through optical means (for example, a splitter, coupler, or the like) from which the temperature measurement is calculated.

A further temperature monitoring system includes a fiber Bragg grating (FBG) optical sensor, which reflects particular wavelengths of light and transmits all others. FBGs are widely used in civil and aerospace structural health monitoring, and have recently been used for biomedical applications. Despite its prevalent use, the FBG sensor is sensitive to both strain and temperature, and the wavelength shift is indiscernible between the two. Several techniques have been proposed to address this issue, such as using two FBGs in the same environment, encapsulating the FBG in a tapered waveguide, and using a plurality of FBGs inscribed on the same fiber. However, these methods are complicated and are not cost effective solutions.

For cryotreatment procedures using a cryoballoon, the systems mentioned above would require the use of a secondary or additional medical device inserted into the patient. Measurement of the tissue temperature with the secondary device would be possible before and after the cryotreatment procedure (for example, cryoablation), or measurement of the temperature of the border of the lesion may be possible during the cryotreatment procedure. However, in this case, artifacts in the temperature measurement might exist if the sensor is located near the cryoballoon. For example, the heat exchange between the cryoballoon and sensor might create a rapid decay of the fluorescence.

Therefore, it is desirable to provide a cryoablation system and device that allows for the real-time lesion formation assessment by providing real-time temperature feedback during a cryotreatment procedure. Lesion quality also depends on the quality of contact between the treatment device and the target tissue. It is further desirable, therefore, to provide a cryoablation system and device that allows for real-time feedback regarding strain on the balloon as it is brought into contact with tissue, as this may be indicative of tissue contact quality.

SUMMARY

The present invention advantageously provides a method and system for identifying an area of ablated tissue and/or assessing contact between a treatment element and tissue and/or assessing occlusion of a body lumen by the treatment element. A device may include an elongate body having a distal portion and a proximal portion, an inflatable treatment element at the distal portion of the elongate body; and at least one fiber sensor, at least a portion of each of the at least one fiber sensor being located within the inflatable treatment element and including at least one singlemode waveguide segment and at least one multimode waveguide segment. For example, the inflatable treatment element may be a cryoballoon. The device may further include a shaft that is slidably disposed within the elongate body, and the shaft may include a distal portion. Each of the at least one fiber sensor including a distal portion and a proximal portion, the distal portion of each of the at least one fiber sensor may be coupled to the distal portion of the shaft. The device may further include a handle coupled to the proximal portion of the elongate body, the handle may have a rotary mechanism, and the proximal portion of each of the at least one fiber sensor may be engaged with the rotary mechanism. Each of the at least one fiber sensor may include a first singlemode waveguide segment, a second singlemode waveguide segment, a third singlemode waveguide segment, a first multimode waveguide segment, and a second multimode waveguide segment. For example, the first multimode waveguide segment may be located between the first and second singlemode waveguide segments and the second multimode waveguide segment may be located between the second and third singlemode waveguide segments. The inflatable treatment element may include an inner surface and the second singlemode waveguide may be configured to be in contact with the inner surface when the inflatable treatment element is inflated. The treatment element may further include an outer surface, which may be configured to be in contact with an area of target tissue when the inflatable element is inflated. Alternatively, each of the at least one fiber sensor may include a first singlemode waveguide segment, a second singlemode waveguide segment, and a multimode waveguide segment, the multimode waveguide segment being located between the first and second singlemode waveguide segments. The inflatable treatment element may include an inner surface and an outer surface, the multimode waveguide being configured to be in contact with the inner surface and the outer surface being configured to be in contact with an area of target tissue when the inflatable treatment element is inflated.

A device may include an elongate body including a distal portion and a proximal portion, an inflatable treatment element at the distal portion of the elongate body, and a first fiber sensor and a second fiber sensor, each of the first and second fiber sensors including a core, at least a portion of each of the first and second fiber sensors being located within the inflatable treatment element and including an area of fiber Bragg grating within the core, the core of the first fiber sensor having a diameter that is different than a diameter of the core of the second fiber sensor.

A medical system for determining a temperature of an area of tissue may include: a device including: an elongate body having a distal portion and a proximal portion; an inflatable treatment element at the distal portion of the elongate body; at least one fiber sensor, at least a portion of each of the at least one fiber sensor being located within the inflatable treatment element and including at least one singlemode waveguide segment and at least one multimode waveguide segment; and a processing unit in communication with the at least one fiber sensor, the processing unit including: a beam processing apparatus configured to receive light transmitted through the at least one fiber sensor; and a hyperspectral imaging and analysis apparatus configured to calculate a temperature of the area of tissue. Each of the at least one fiber sensor may include a first singlemode waveguide segment, a second singlemode waveguide segment, a third singlemode waveguide segment, a first multimode waveguide segment, and a second multimode waveguide segment. The first multimode waveguide segment may be located between the first and second singlemode waveguide segments and the second multimode waveguide segment may be located between the second and third singlemode waveguide segments. The inflatable treatment element may include an inner surface and an outer surface, the second singlemode waveguide being configured to be in contact with the inner surface and the outer surface being configured to be in contact with the area of tissue when the inflatable treatment element is inflated. Alternatively, each of the at least one fiber sensor may include a first singlemode waveguide segment, a second singlemode waveguide segment, and a multimode waveguide segment, the multimode waveguide segment being located between the first and second singlemode waveguide segments. The inflatable treatment element may include an inner surface and an outer surface, the multimode waveguide being configured to be in contact with the inner surface and the outer surface being configured to be in contact with an area of target tissue when the inflatable treatment element is inflated. The system may further include a light source configured to transmit light to the at least one fiber sensor.

A method for determining whether an area of tissue has been ablated may include: placing a medical device in contact with the area of tissue, the medical device including an inflated treatment element and a fiber sensor, the a fiber sensor including at least one singlemode waveguide segment and at least one multimode waveguide segment located within the inflated treatment element, an outer surface of the inflated treatment element being in direct contact with the area of tissue and at least one of the at least one singlemode waveguide segment and the at least one multimode waveguide segment being in direct contact with an inner surface of the inflated treatment element that corresponds to the outer surface of the inflated treatment element that is in direct contact with the area of tissue; transmitting through the fiber sensor light emitted by the area of tissue with which the inflated treatment element is in direct contact; and receiving the transmitted light with a processing unit, the processing unit being configured to: correlate the received light with a temperature of the tissue from which the light was emitted; and determine whether the area of tissue is ablated based at least in part on the temperature correlation.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

The present invention relates to a device, system, and method for identifying an area of ablated tissue. The present invention also relates to a device, system, and method for assessing contact between a treatment element and tissue and/or assessing occlusion of a body lumen by the treatment element. Specifically, the device, system, and method may include one or more fiber sensors and a processing unit for receiving emitted and/or reflected light from tissue and making one or more determinations based on the received light regarding ablated tissue, tissue contact, and/or occlusion.

Figure 1:
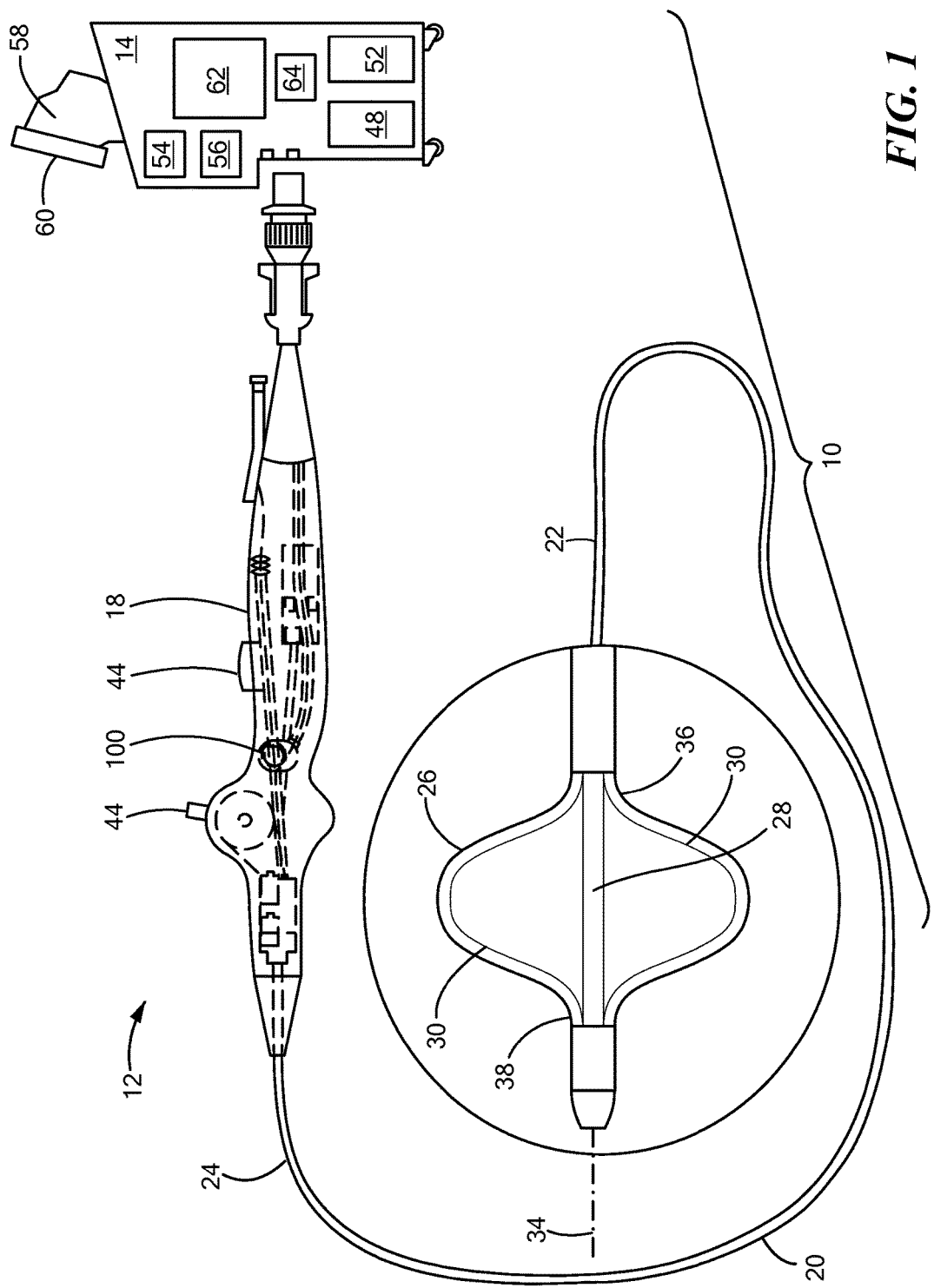
FIG. 1 shows an exemplary cryotreatment system that includes a device having at least one fiber sensor.

Referring now to FIG. 1, an exemplary cryotreatment system that includes a device having a fiber sensor for monitoring tissue temperature is shown. The system 10 may generally include a treatment device, such as a cryotreatment catheter 12, for thermally treating an area of tissue, and a console 14 that houses various system 10 controls. The system 10 may be adapted for a cryotreatment procedure, such as cryoablation. The system 10 may additionally be adapted for radiofrequency (RF) ablation and/or phased RF ablation, ultrasound ablation, laser ablation, microwave ablation, hot balloon ablation, or other ablation methods or combinations thereof.

Figure 2:
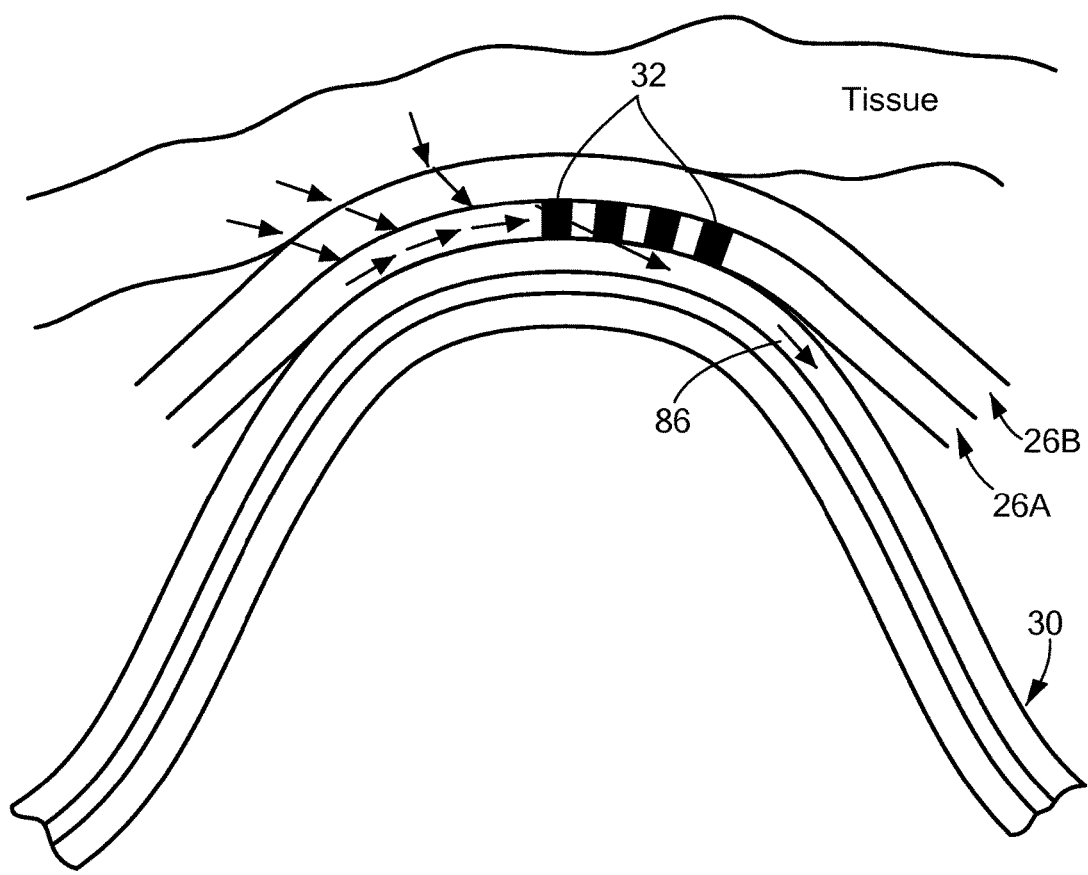
FIG. 2 shows a close-up, cross-sectional view of a cryotreatment device in contact with tissue and light passing from the tissue into the fiber sensor.
Figure 7:
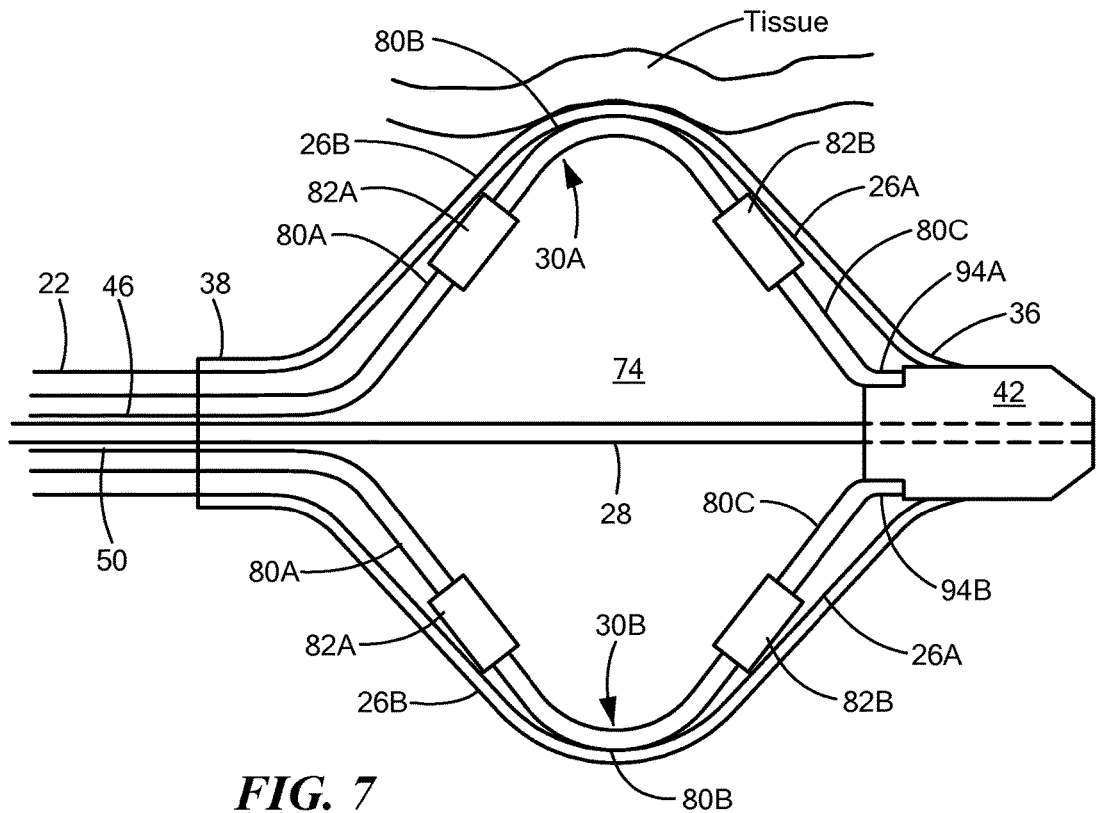
FIG. 7 shows a cross-sectional view of a cryotreatment device having a first fiber sensor and a second fiber sensor according to a first embodiment, the cryotreatment device positioned in direct contact with an area of tissue.

The cryotreatment catheter 12 may generally include a handle 18, an elongate body 20 having a distal portion 22 and a proximal portion 24, one or more inflatable treatment elements such as a cryoballoon 26, a shaft 28 (for example, a guidewire lumen), and one or more fiber sensors 30, which may be referred to herein as "waveguides." Further, the cryotreatment catheter 12 may have a longitudinal axis 34. The treatment element may be a cryoballoon 26 coupled to the distal portion 22 of the elongate body 20 of the cryotreatment catheter 12. For example, the cryoballoon 26 may define a proximal portion or neck 36 that is affixed to or coupled to the distal portion 22 of the elongate body 20, and may further define a distal portion or neck 38 that is affixed to or coupled to the shaft 28 (such as the distal portion 40 of the shaft 28). However, it will be understood that the cryoballoon 26 may be coupled, affixed, disposed on, integrated with, or otherwise attached to the elongate body 20 and/or the shaft 28. Additionally, multiple cryoballoons may be used, such as when the cryoballoon 26A is disposed within a second cryoballoon 26B (as shown in FIG. 7). Further, as shown in FIG. 2, the inner cryoballoon 26A may include long-period grating (LPG) 32 inscribed on it mechanically or chemically, such as by photoinscribing, etching, or the like. The length and period of the grating 32 may be optimized to couple light at a particular wavelength from the outer cryoballoon 26B to the cladding mode of the fiber sensor 30. The emitted and/or reflected light from the tissue may be refracted totally or partially through the outer cryoballoon 26B. Depending on the incident angle, the light may propagate through the inner cryoballoon 26A. At the grating, the light may be coupled to the cladding modes of the fiber sensor 30 (for example, as depicted with arrows in FIG. 2). The grating may be designed to provide multiple wavelengths resonance or an arbitrary spectral shape response. Although the cryotreatment catheter 12 is shown in the figures as being in contact with tissue on only one side of the cryoballoon 26, it will be understood that the device 12 may be positioned within a body lumen, such that the circumference of the cryoballoon 26 is in contact with tissue.

The shaft 28 may lie along the longitudinal axis 34 and be longitudinally movable or slidable within the elongate body 20. In this manner, longitudinal movement of the shaft 28 will affect the shape of the cryoballoon 26. The proximal portion of the shaft 28 may be in mechanical communication with one or more steering mechanisms 44 in the handle 18 of the cryotreatment catheter 12, such that the shaft 28 may be longitudinally extended or retracted using one or more steering mechanisms 44, such as knobs, levers, wheels, pull cords, and the like.

In addition to the shaft 28, the cryotreatment catheter 12 may include one or more lumens. As shown in FIG. 7, the cryotreatment catheter 12 may include a refrigerant injection lumen 46 in fluid communication with a refrigerant supply reservoir 48, and a refrigerant recovery lumen 50 in fluid communication with a refrigerant recovery reservoir 52. Further, the refrigerant recovery lumen 50 may be in communication with a vacuum 54 to facilitate removal of fluid from the cryoballoon 26 (for example, expanded refrigerant). If the cryotreatment catheter 12 includes thermoelectric cooling elements or electrodes capable of transmitting radiofrequency (RF), ultrasound, microwave, electroporation energy, or the like, the elongate body 18 may include a lumen in electrical communication with an energy generator 56.

The console 14 may be in electrical and fluid communication with the cryotreatment catheter 12 and may include one or more fluid (for example, cryotreatment refrigerant)

reservoirs 48, refrigerant recovery reservoirs 52, energy generators 56, and computers 58 with displays 60, and may further include various other screens, user input controls, keyboards, buttons, valves, conduits, connectors, power sources, processors, and computers for adjusting and monitoring system 10 parameters. As used herein, the term "computer" may refer to any programmable data-processing unit, including a smart phone, dedicated internal circuitry, user control device, or the like. The computer 58 may be in electrical and/or wireless communication with a processing unit 62 that is in optical communication with the one or more fiber sensors 30. Although the processing unit 62 is shown in FIG. 1 as being located within the console 14, it will be understood that the processing unit 62 may alternatively be located external to the console 14. The computer 58 may further be in communication with the one or more treatment elements 26 and one or more system valves (not shown). The processing unit 62 and/or the computer may be programmable to execute an algorithm for calculating at least tissue temperature and cryoballoon strain and for generating one or more displays or alerts to notify the user of various system criteria or determinations. As a non-limiting embodiment, the proximal portion of the cryotreatment catheter 12 may include an electrical connection that is matable to at least a portion of the console (for example, with the electrophysiology recording equipment) and in electrical communication with the processing unit 62.

Figure 3A:
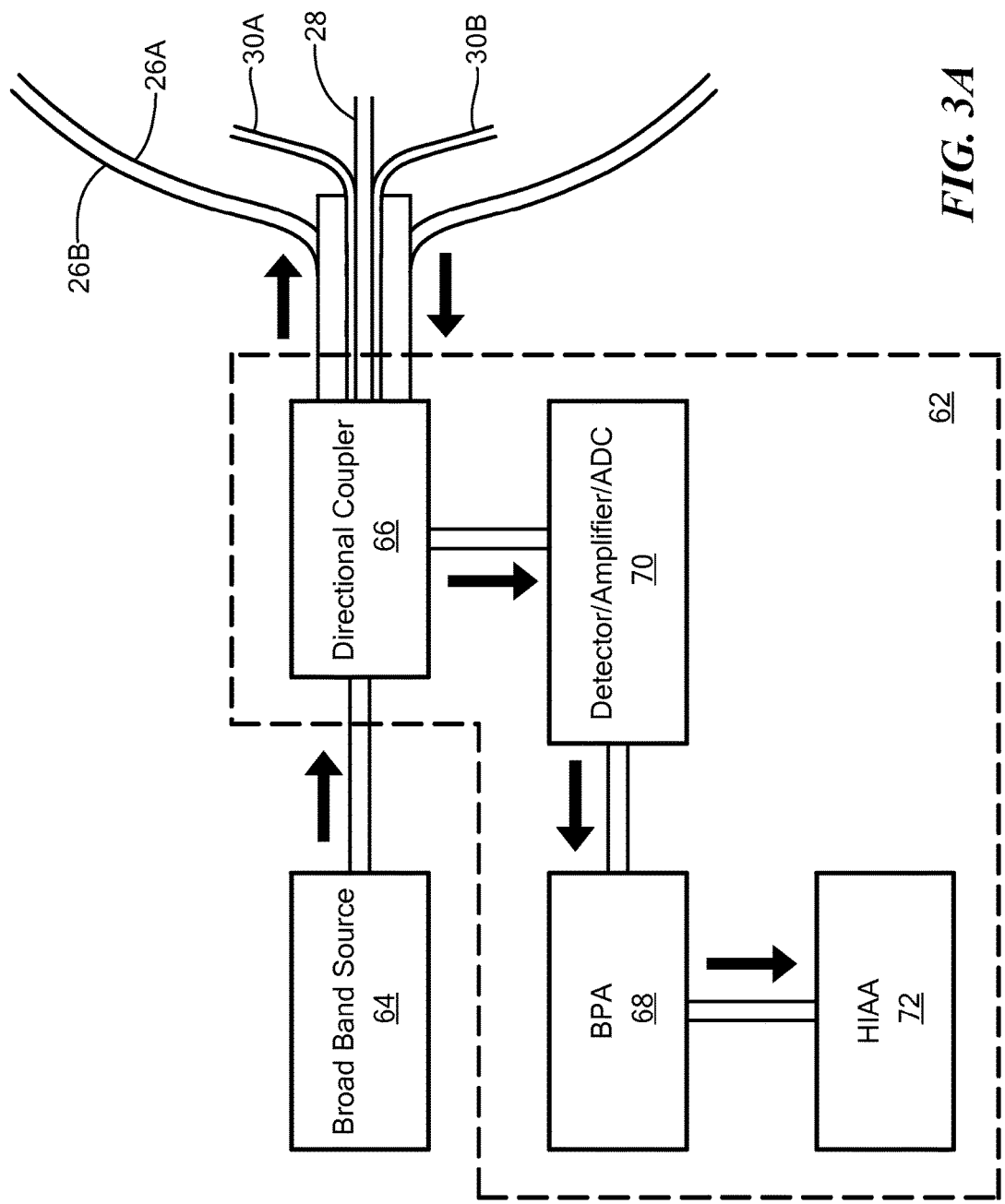
FIG. 3A shows a schematic view of a first exemplary processing unit and light source.
Figure 3B:
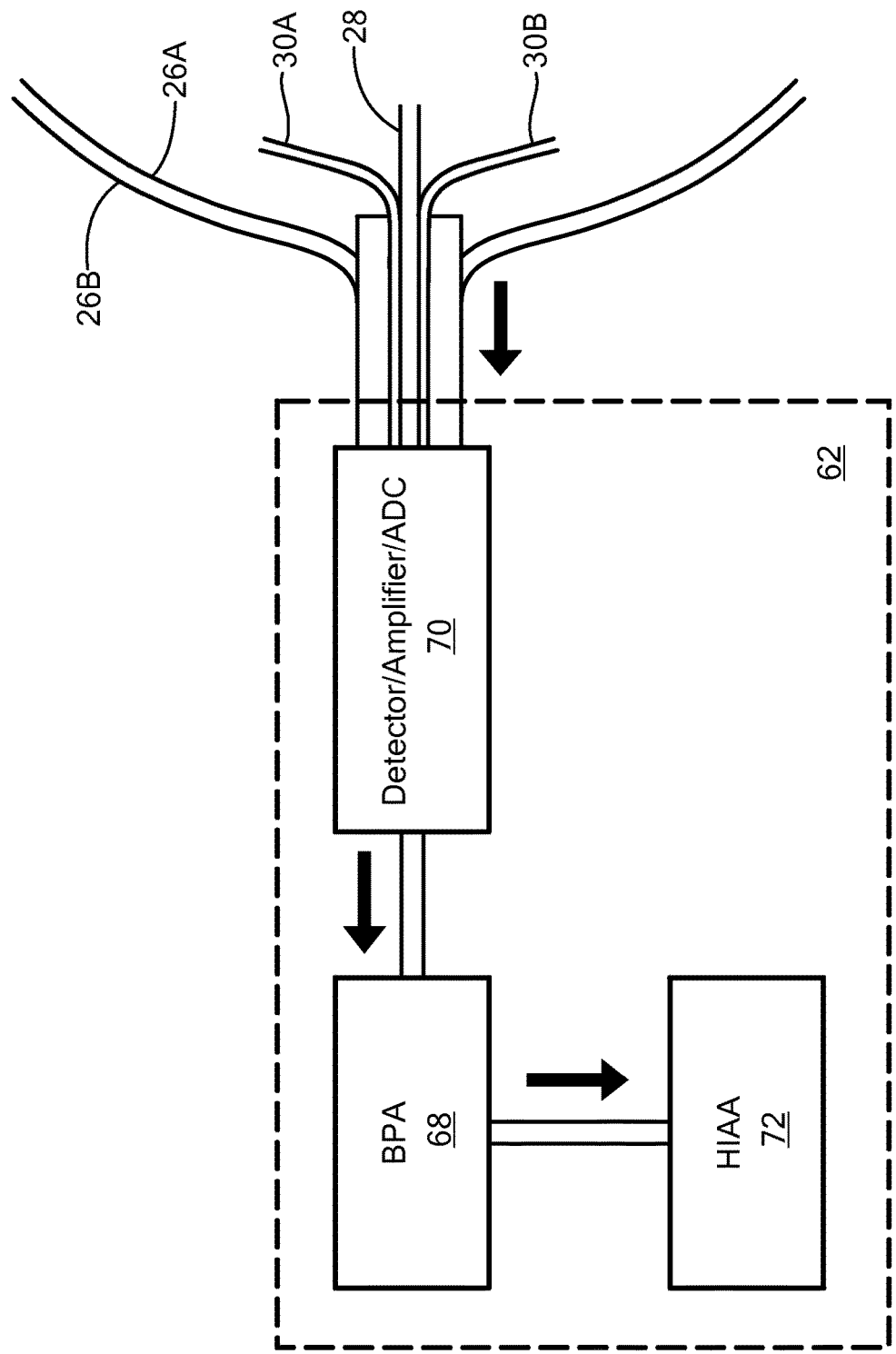
FIG. 3B shows a schematic view of a second exemplary processing unit without a light source.

Specifically, as is shown in FIG. 3A, the console 14 may optionally include a light source 64 (such as a broadband light source or laser optical source) that directs light through the one or more fiber sensors 30 and a directional coupler 66, although light may be transmitted from the one or more fiber sensors 30 to the processing unit 62 without the use of a light source 64, as shown in FIG. 3B. For example, the one or more fiber sensors 30 may receive and transmit light that is naturally emitted from the tissue without the use of a light source. That is, the light received and transmitted by the one or more fiber sensors may be emitted from (or produced by) the tissue rather than light that is delivered from a light source and reflected, refracted, and/or scattered by the tissue. As is described in more detail below, light that is emitted and/or reflected from tissue may travel back through the one or more fiber sensors 30, through the directional coupler 66, through a detector/amplifier/analog-to-digital converter (ADC) 70, and into a beam processing apparatus (BPA) 68. Data from the BPA 68 may then be transmitted to a hyperspectral imaging and analysis apparatus (HIAA) 72 for temperature and strain measurement.

However, use of the light source 64 is optional because the fiber sensor 30 of the device may be configured to detect a thermal contrast between ablated tissue and non-ablated tissue through evanescent coupling without the need for a light source. The thermal contrast may be discernible despite the scattering and absorption by blood. Via evanescent coupling, electromagnetic waves are transmitted from the tissue to the fiber sensor 30 (through the one or more cryoballoons 26) by means of the evanescent, exponentially decaying electromagnetic field. The cryoballoon 26 (or outer cryoballoon if more than one cryoballoon is used) is positioned in direct contact with tissue, thus placing the fiber sensor 30 in very close proximity to the tissue. The fiber sensor 30 is configured to support modes (or light wave propagation pattern) of the appropriate frequency that is emitted from the tissue, and the emitted light is thereby connected or coupled to the fiber sensor 30. Additionally, because the HIAA 72 is able to calculate temperature based on data from the BPA 68, thermocouples or other temperature-sensing components are not required to differentiate between ablated tissue and non-ablated tissue. This may simplify the device and system, and may also allow for smaller device design.

Although not shown, the console 14 may also include one or more valves that are in electrical and/or mechanical communication with, and controllable by, the console 14. For example, the computer 58 and/or processing unit 62 may be programmable to control various system components, such as the one or more valves, to operate according to a duty cycle that includes opening and closing the one or more valves to regulate the flow of refrigerant through the system 10 and the catheter 12, and to thereby regulate the temperature of the cryoballoon 26. The duty cycle may be programmable by the user and/or may be automatically set by the console 14 according to a predicted tissue temperature based at least in part on signals from the one or more fiber sensors 30.

As discussed above, the cryotreatment catheter 12 may include a cryoballoon 26 having a proximal neck 36 coupled to the distal portion 22 of the elongate body 20 and a distal neck 38 coupled to the distal portion 40 of the shaft 28. The distal portion 40 of the shaft 28 may also be coupled to or integrated with a distal tip 42, and the distal neck 38 may be coupled to the distal tip 42. However, it will be understood that the cryoballoon 26 may be coupled to the elongate body 20 and/or shaft 28 in other suitable configurations. Further, FIGS. 7, 8, 10, 12, and 13 show an embodiment in which the treatment element includes an inner cryoballoon 26A and an outer cryoballoon 26B. Such a configuration may enhance patient safety, as the outer balloon may prevent refrigerant from entering the patient's bloodstream if the inner balloon developed a leak. The cryoballoon 26, or the inner cryoballoon 26A in the two-balloon configuration, may also define an inner chamber 74 in which refrigerant is expelled from the fluid injection lumen 46 through one or more injection elements 76. For example, the injection element 76 may include a conduit that is wrapped around the shaft 28 in one or more coils, and may have a plurality of injection apertures (not shown). Refrigerant expelled into the inner chamber 74 may be drawn from the chamber 74 and into the fluid recovery lumen 50 by the negative pressure environment generated by the vacuum 54, with which the fluid recovery lumen 50 may be in fluid communication. Recovered refrigerant may be vented to the atmosphere or collected in the refrigerant recovery reservoir 52. Although the treatment element 26 is shown and described herein as being a cryoballoon 26, it will be understood that the treatment element 26 may be any structure capable of ablating tissue and retaining refrigerant within.

Figure 5A:
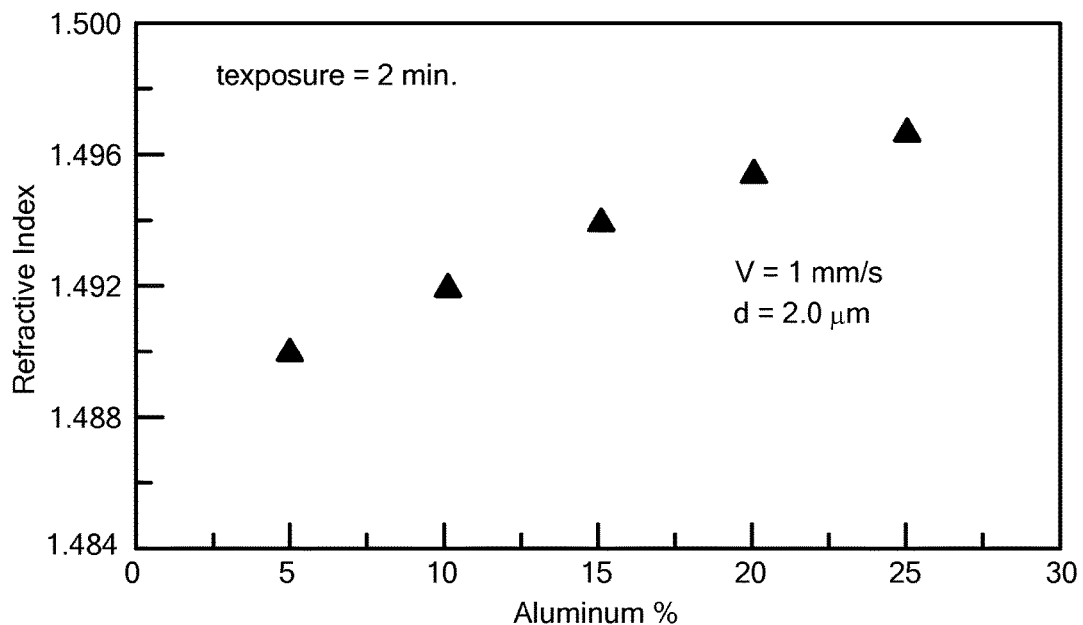
FIGS. 5A and 5B show dependence of the refractive index of a material on the percent composition of aluminum (Al) and zirconium (Zr), respectively.
Figure 5B:
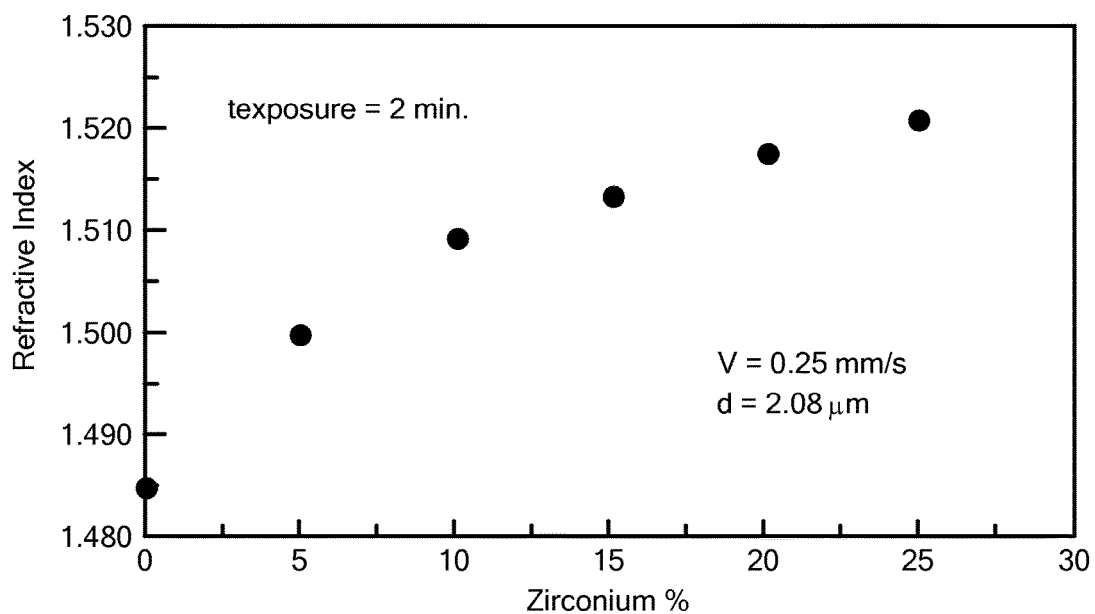

The one or more fiber sensors 30 may transmit light from ablated tissue, such as radiated, emitted, scattered, and/or reflected light, to the console 14 for processing and analysis by the processing unit 62. As a non-limiting example, the one or more fibers 30 may be composed of materials known in the art to be suitable for fiber optics applications, including but not limited to a polyglass-based sol-gel material. Hybrid $(1-x)SiO_2-xZrO_2$, $(1-x-y)SiO_2-xAl_2O_3-yP_2O_5$, and $(1-y)SiO_2-7yAl_2O_3$ sol-gel solutions may be prepared using Methaciyloxypropyltrioxysilane (MAPTMS) hydrolyzed with 1.5 equivalents of $H_2O$, and with 0.1 M HCl as a catalyst. Further, $Zr(OC_3H_7)_4$, which may be used as a refractive index modifier, may be dissolved in isopropanol in a 1:1 volume ratio and then the mixture may be added dropwise to the stirred solution of the partially hydrolyzed MAPTMS. After adding water to complete the hydrolyzation of alkoxide substituents, Irgacure 184 (Ciba Specialty Chemicals Inc., Basel, Switzerland) may be introduced as a photoinitiator. The adjustment of chemical composition of the raw materials, ultraviolet light exposure, and heat treatment provides precise selection of refractive index from 1.48 to 1.52 at a wavelength of 632.8 nm. This organically modified glass fabric belongs to the class of hybrid organic-inorganic glasses known variously as "ormocers" (organically modified ceramics), "ormosils" (organically modified silicates), "ceramers," "polycerams," or simply hybrid sol-gel glasses (HSGG). Optical devices may be rapidly prototyped with HSGG because (1) homogenous thick films can be precision deposited without cracks in a single step; (2) a large menu of organically modified materials may be synthesized to quickly adapt to specific device requirements; and (3) HSGGs offer a singular advantage in being able to resolve conflicting material demands of the device. The essence of this flexibility may be found in the coupling of the attractive features of organic polymers with those of inorganic glasses. FIGS. 5A and 5B depict the dependence of the refractive index of the films on the percentage composition of aluminum (Al) and zirconium (Zr), respectively. The fiber sensor 30 may be made using one or more variants of the HSGG material to have the refractive indices tuned to optimize light coupling from the tissue.

Figure 4A:
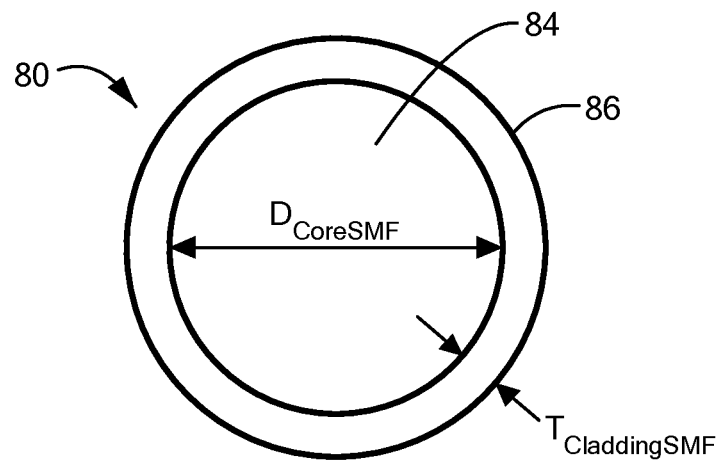
FIG. 4A shows a cross-sectional view of a singlemode fiber.
Figure 4B:
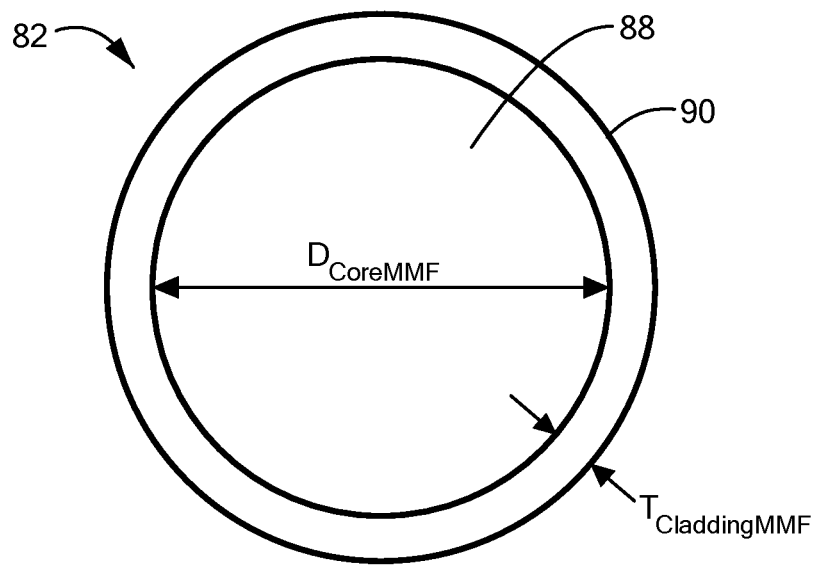
FIG. 4B shows a cross-sectional view of a multimode fiber.
Figure 8:
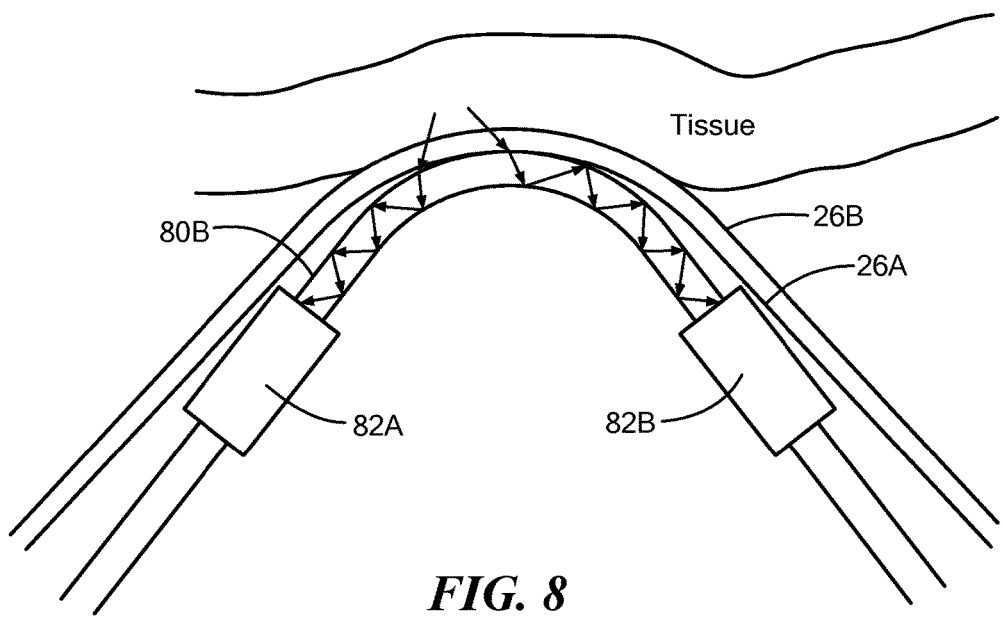
FIG. 8 shows a cross-sectional view of a portion of the cryotreatment device of FIG. 7.
Figure 10:
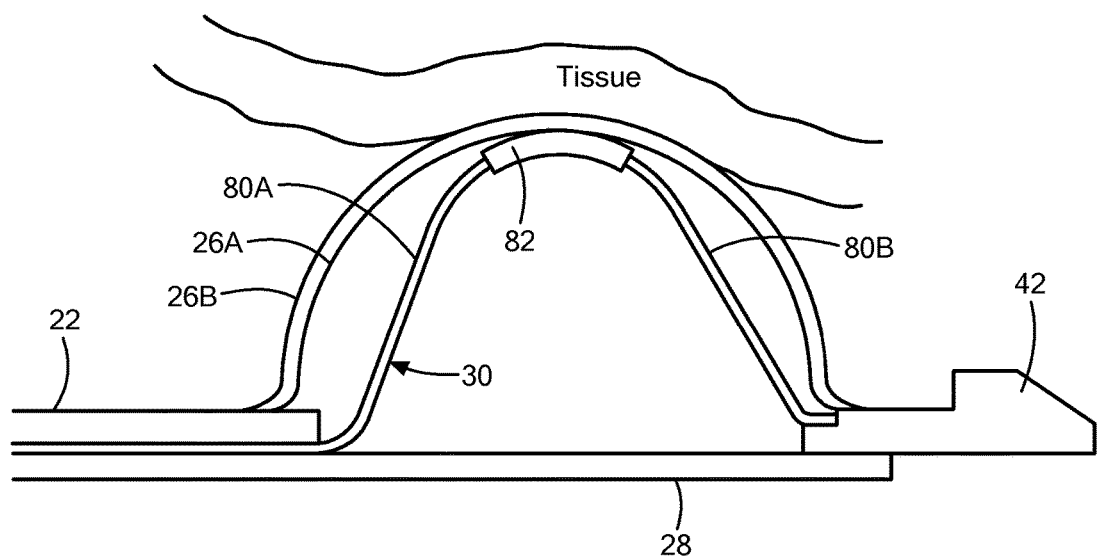
FIG. 10 shows a cross-sectional view of a portion of a cryotreatment device having at least one fiber sensor according to a second embodiment, the cryotreatment device positioned in direct contact with an area of tissue.

As discussed above, the fiber sensor 30 of the device may be configured to detect a thermal contrast between ablated tissue and non-ablated tissue through evanescent coupling. Each fiber sensor 30 may be a singlemode-multimode-singlemode (SMS) fiber structure that includes at least one step index singlemode (SMF) waveguide segment 80 and at least one step index multimode (MMF) waveguide segment 82 (for example, as shown in FIGS. 7, 8, and 10). Alternatively, the fiber sensor 30 may be a SMF waveguide (for example, as shown in FIG. 2). As shown in FIG. 4A, the SMF waveguide 80 may have a core 84 having a diameter $D_{CoreSMF}$, a cladding 86 having a thickness $T_{claddingSMF}$, a length, and a difference refractive index (cladding refractive index/core refractive index) optimized for maximum evanescent field coupling coefficient. Likewise, as shown in FIG. 4B, the MMF waveguide 82 may have a core 88 having a diameter $D_{CoreMMF}$, a cladding 90 having a thickness $T_{claddingMMF}$, a length, and a difference refractive index optimized for maximum coupling of modes from SMF waveguide to core and cladding modes of the MMF waveguide. The diameter $D_{coreMMF}$ of the MMF waveguide core 88 may be larger than the diameter $D_{coreSMF}$ of the SMF waveguide core 84. The MMF waveguide 82 may be fusion spliced to the SMF waveguide 80 so as to minimize optical loss.

Figure 6:
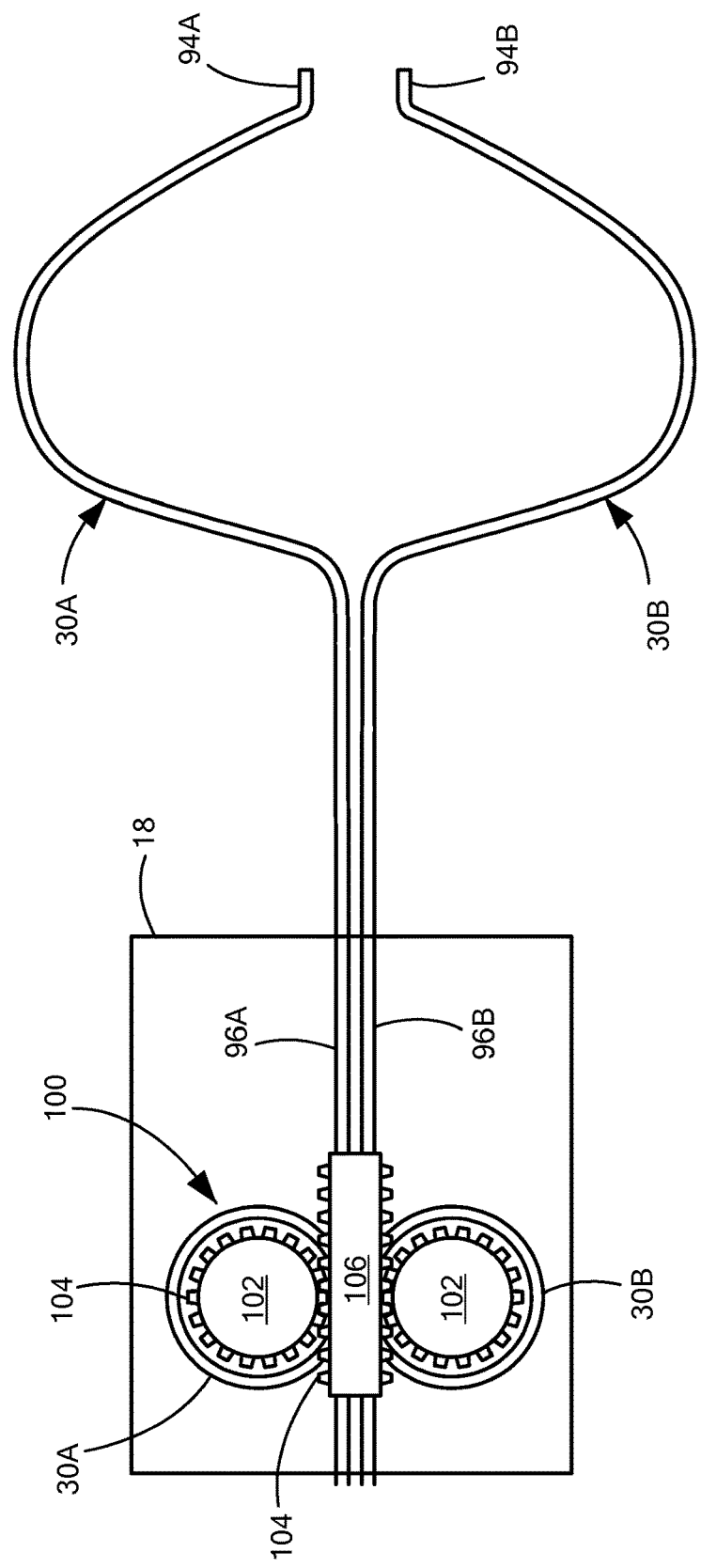
FIG. 6 shows a first fiber sensor and a second fiber sensor coupled to a rotary mechanism, the rotary mechanism located within a device handle.

The cryotreatment catheter 12 may have a first fiber sensor 30A and a second fiber sensor 30B that are diametrically positioned within the inner chamber 74. The distal portion 94A, 94B of each fiber sensor 30A, 30B, respectively, may be attached to a portion of the shaft 28, for example, at a location at or proximate the distal portion 40. In contrast, the proximal portion 96A, 96B of each fiber sensor 30A, 30B, respectively, may not be coupled to the shaft 28 and instead may freely move longitudinally within the inner chamber 74 and the elongate body 20. For example, the proximal portions 96A, 96B may be coupled to or otherwise engaged with a rotary mechanism 100 located within the handle 18 (shown in FIG. 6). The rotary mechanism 100 may allow longitudinal movement of the fiber sensors 30A, 30B within the inner chamber 74 and the elongate body 20 as the balloon is inflated and deflated while maintaining a tension in the fiber sensors 30A, 30B so they do not buckle, bunch, or interfere with the cryotreatment procedure. As a non-limiting example, the rotary mechanism 100 may include a spool 102 for each fiber sensor 30A, 30B. Each fiber sensor 30A, 30B may be wound about a spool 102, and the spools 102 may include teeth or protrusions 104 that may be interdigitated with teeth or protrusions 104 on a base unit 106. As the spools 102 are rotated, the fiber sensors 30A, 30B may be wound or unwound about the spools 102.

Blood includes several components, including plasma (typically about 55% total volume), white blood cells and platelets (typically less than 1% total volume), and red blood cells (typically about 45% total volume). The typical composition of plasma is about 92% water, about 7% proteins, and about 1% mineral salt, sugars, fats, and hormones. Imaging or sensing through blood is driven by the optical characteristics of blood: (1) absorption of radiation by hemoglobin and water; and (2) scattering of radiation by red blood cells. There are wavelength ranges (1.4-1.8 microns, 2.1-2.4 microns, 3.7-4.3 microns, 4.6-5.4 microns, and 7-14 microns) at which the desirable characteristics of low scattering of light by suspended red blood cells and low absorption of radiation by hemoglobin and water occur. Thus, the light source 64 may be used to transmit light to the one or more fiber sensors 30 at a wavelength within one or more of these ranges. Alternatively, the system may include only a processing unit 62 configured to sense reflected/emitted light from tissue without the light source 64 (for example, as shown in FIG. 3B). It has been shown that ablated tissue (that is, immediately after ablation and before temperature homogenization) exhibits high thermal contrast compared to surrounding unablated tissue and provides enough radiation to be sensed by off-the-shelf high-sensitivity bolometers without the aid of an external light source.

Figure 9:
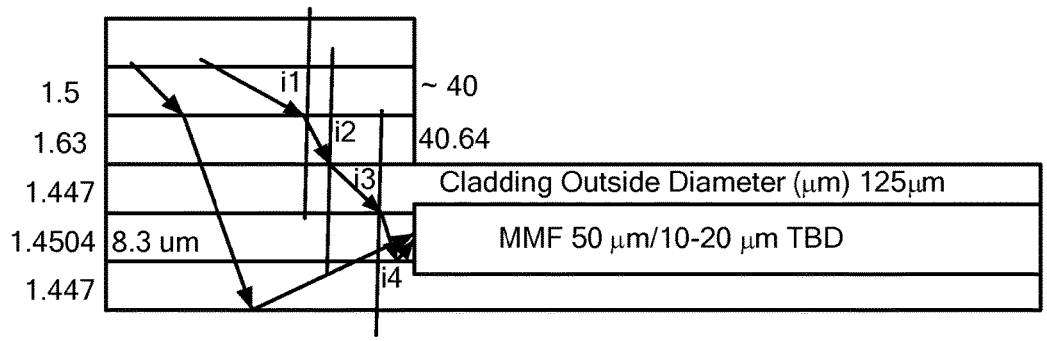
FIG. 9 shows movement of light from tissue through a series of materials and into a core of multimode fiber segment.

FIG. 7 shows an exemplary placement of a two-cryoballoon treatment element in direct contact with target tissue for receiving emitted and/or reflected light from the tissue through evanescent coupling. Having the balloons 26A, 26B inflated during sensing may minimize the effect of blood flow around the measured tissue. When the treatment element is in contact with the tissue, the tissue, the outer cryoballoon 26B, the inner cryoballoon 26A, and the fiber sensor 30 may form a stack of layers of varying refractive indices, as shown in FIG. 9. As a non-limiting example for illustration, the outer cryoballoon 26B may be composed of polyurethane with a refractive index of 1.5 measured at wavelength 632.8 nm and the inner cryoballoon 26A may be composed of polyethylene terephthalate having a refractive index of 1.63 measured at wavelength 632.8 nm. The SMF waveguide cladding 86 may have a refractive index of, for example, 1.447 and the SMF waveguide cladding 88 may have a refractive index of approximately 1.4504. Non-limiting thicknesses of the cladding, cores, and cryoballoons are shown in FIG. 9 for illustration only. The outer cryoballoon 26B and/or inner cryoballoon 26A may be selected to have a refractive index for optimal refraction of one or more spectra of interest and may be different than the exemplary characteristics shown in FIG. 7.

As shown in FIGS. 8 and 9, the light emitted or radiated from the tissue may be first refracted in total or in part through the outer cryoballoon 26B to the inner cryoballoon 26A, and then to, for example, the cladding 86 of the SMF waveguide 80. The cladding modes in the SMF waveguide 80 may enter the core of the MMF waveguide 82. For example, the cryotreatment catheter 12 may include a first MMF waveguide segment 82A at a location proximal to the SMF waveguide segment 80B being in contact with the target tissue (through cryoballoons 26A, 26B) and a second MMF waveguide segment 82B at a location distal to the SMF waveguide segment 80C being directed toward the target tissue. Put another way, the first MMF waveguide segment 82A may be located between a first 80A and a second 80B SMF waveguide segment and the second MMF waveguide segment 82B may be located between the second 80B and a third 80C SMF waveguide segment (as shown in FIG. 7).

The light may then travel through the fiber sensor 30 to the console 14. Specifically, the light (electromagnetic radiation) may pass through the directional coupler 66 and into the BPA 68. The BPA 68 may include a grating, broadband infrared detector (such as a combination of a bolometer and III-V semiconductor detector), and readout electronics such as a converter circuit, signal sampling, and signal integrity multiplexer. For example, a bolometer in the BPA 68 may measure the power of the incident electromagnetic radiation (light). The BPA 68 may convert the optical signal to an electrical signal including a plurality of pixels and perform signal processing (for example, non-uniformity correction, coarse pixel correction, and cross-talk reduction). Further, the BPA 68 may correlate each pixel to a value of a spectrum of light. The signal of each pixel in the form of a spectrum may then be transmitted to the HIAA 72 for temperature measurement using a thermography technique and/or spectral analysis. For example, a temperature measurement range of between approximately −100° C. to approximately 80° C. may be achievable using thermography. The HIAA 72 may process radiation in the long-infrared range of the electromagnetic spectrum to determine "hot spots," or areas of tissue having a higher heat signature. Tissue ablated using cryoablation will register a lower heat signature than areas of non-ablated tissue. Further, the HIAA 72 may compare acquired spectral data to reference spectral data. For example, the HIAA 72 may compare the spectrum of each pixel to a reference spectrum of an ablated tissue. The processing unit 62 may communicate this data to the user, such as by displaying a heat signature map, hyperspectral image of the tissue, and/or spectral data. The HIAA 72 may further be programmed or programmable to execute one or more algorithms that allows for compensation for motion caused by the beating heart.

Temperature measurements may be taken throughout the cryotreatment procedure. However, temperature measurements taken during the treatment portion of the procedure, such as when tissue is ablated, will reflect the temperature within the balloon rather than tissue temperature. This is because during ablation the liquid refrigerant undergoes a physical state transformation once injected into the inner chamber 74. Tissue temperature may be accurately measured during an inflation phase before ablation and during a thawing phase after ablation. For example, the treatment element may remain inflated after ablation while the treatment element undergoes a thawing phase. During the thawing phase, the refrigerant injection lumen may be closed by one or more valves and the refrigerant expansion may be controlled by a proportional valve (not shown). Thus, there may not be any gas turbulences within the inner chamber 74 to affect the tissue temperature measurement.

Referring now to FIG. 10, a further embodiment of a cryotreatment catheter is shown. The cryotreatment catheter 12 may include one or more fiber sensors 30 each including a first singlemode fiber (SMF) waveguide segment 80A and a second singlemode fiber (SMF) waveguide segment 80B. The first 80A and second 80B SMF waveguide segments may be connected by a multimode fiber (MMF) 82 through a coupling surface such as a permanent welding joint between the fibers (for example, a fusion splice) or a pigtail connection (FC/PC connections). The first SMF waveguide segment 80A may convey light into the core 88 and cladding 90 of the MMF 82. The SMF waveguide segments 80A, 80B and the MMF 82 may each be step index fibers. Further, the MMF waveguide 82 may be the portion of the fiber sensor 30 that is brought into contact with the target tissue (through the inner cryoballoon 26A and the outer cryoballoon 26B). The distal portion 94 of the fiber sensor 30 may be coupled to the shaft 28 within, for example, the inner cryoballoon 26A, and the proximal portion 96 may be coupled to a rotary mechanism 100, as is shown and described in FIG. 6.

Light emitted from the light source 64 may be conveyed by the first SMF waveguide segment 80A into the core 88 and cladding 90 of MMF waveguide 82, and then may be conveyed to the second SMF waveguide segment 80B as a result of interference. The second SMF waveguide segment 80B may be polished and treated for maximum reflection. As per reciprocity, the reflected light may then be subject to the same optical path. Light reflected from the second SMF waveguide segment 80B may then excite the core 88 and cladding 90 of the MMF waveguide 82 and then be conveyed into the first SMF waveguide segment 80A. The transmitted light is wavelength dependent. Further, an isolator may be used to prevent reflected light from interfering with the light source 64. The directional coupler 66 may guide the reflected light toward the BPA 68 to process the conveyed light.

Figure 11:
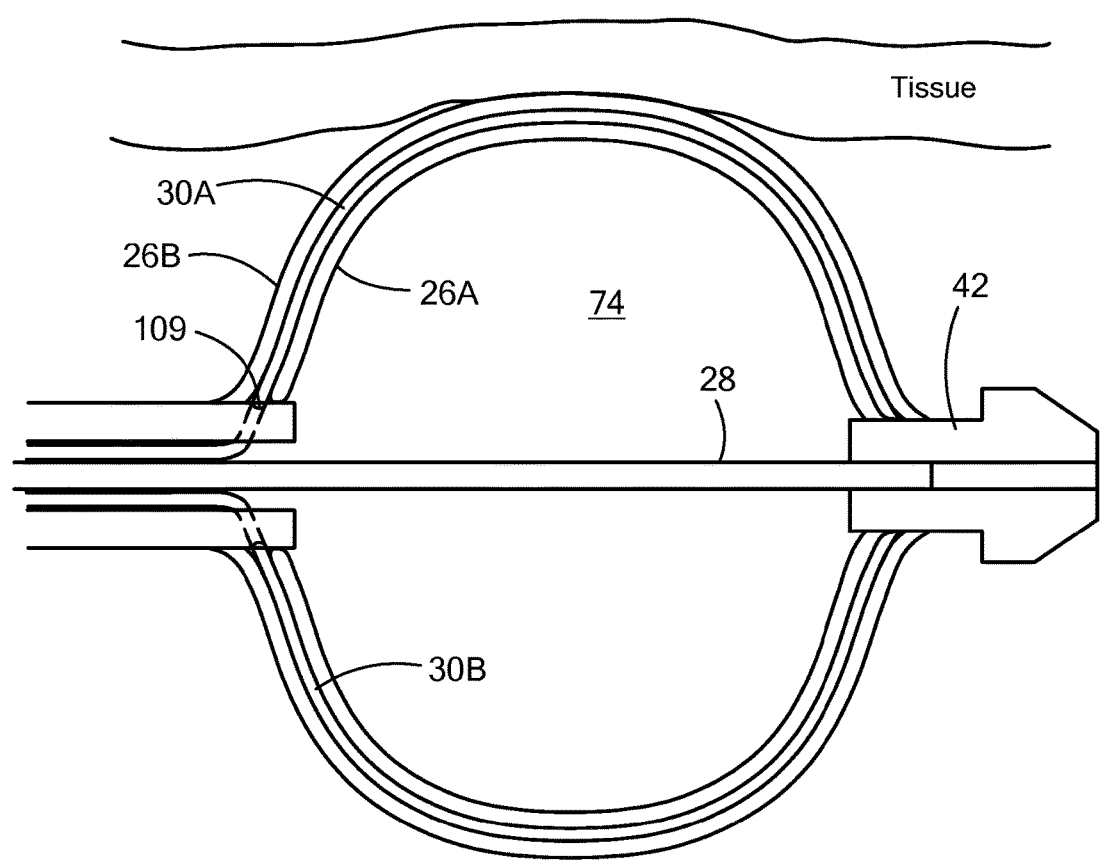
FIG. 11 shows a cross-sectional view of a portion of a cryotreatment device having at least one fiber sensor located between a first and a second cryoballoon according to a third embodiment, the cryotreatment device positioned in direct contact with an area of tissue.

Referring now to FIG. 11, a further embodiment of a cryotreatment catheter is shown. The cryotreatment catheter 12 may include one or more fiber sensors 30, which may include one or more SMF waveguide segments 80 and one or more MMF waveguide segments 82 (for example, as shown in FIGS. 7, 8, and 10) or the one or more fiber sensors 30 may be composed of a single SMF waveguide or a single MMF waveguide. Regardless of the configuration of the one or more fiber sensors 30, the one or more fiber sensors 30 may be located between the inner (first) cryoballoon 26A and the outer (second) cryoballoon 26B. For example, as shown in FIG. 11, each of the first 30A and second 30B fiber sensors may pass through the elongate body 20 and exit the elongate body 20 through an aperture 109 in the side wall of the elongate body 20 that is located between the proximal neck 36A of the inner cryoballoon 26A and the proximal neck 36B of the outer cryoballoon 26B. The distal portion of each of the fiber sensors 30A, 30B maybe coupled to the distal portion of the shaft 28 and/or the distal tip 42. Positioning the fiber sensors 30A, 30B between the inner 26A and outer 26B cryoballoons may not only eliminate gas turbulence caused by the circulation of refrigerant within the inner chamber 74, this configuration allows the fiber sensors 30A, 30B to be located closer to the tissue, which may enhance the optical coupling from the tissue to the fiber sensors 30A, 30B. Although a space or gap is shown between the fiber sensors 30A, 30B and the inner 26A and outer balloons 26B for the sake of illustration, it will be understood that at least a portion of each fiber sensor 30A, 30B may be in contact with both the inner balloon 26A and the outer balloon 26B.

Referring now to FIGS. 12-14B, a further embodiment of a cryotreatment device is shown. The cryotreatment device 12 including one or more fiber sensors 30 may also be used to detect strain on the one or more cryoballoons 26 during a procedure, which may indicate tissue contact and occlusion status. For example, strain data may indicate whether a treatment element is fully occluding a pulmonary vein ostium and/or whether there is sufficient contact between the treatment element and tissue. When the one or more cryoballoons 26 are pushed against tissue, contact is indicated by the resulting deformation in the one or more fiber sensors 30. If there is no contact between the one or more cryoballoons 26 and tissue, there will also be no resulting deformation.

When the one or more cryoballoons 26 are inflated and the one or more fiber sensors 30 are deflected from the device's longitudinal axis 34 during use (as shown, for example, in FIGS. 12 and 13), the bend in each fiber sensor 30 causes the refractive index distribution of the fiber sensor 30 may no longer be symmetric. As a result, the spectrum may shift to shorter wavelengths as the bend increases. Once the cryoballoon(s) is/are buckled, any stress on the cryoballoon(s) by the tissue may affect the curvature, which may be directly measured by an increase of spectral response amplitude.

Figure 12:
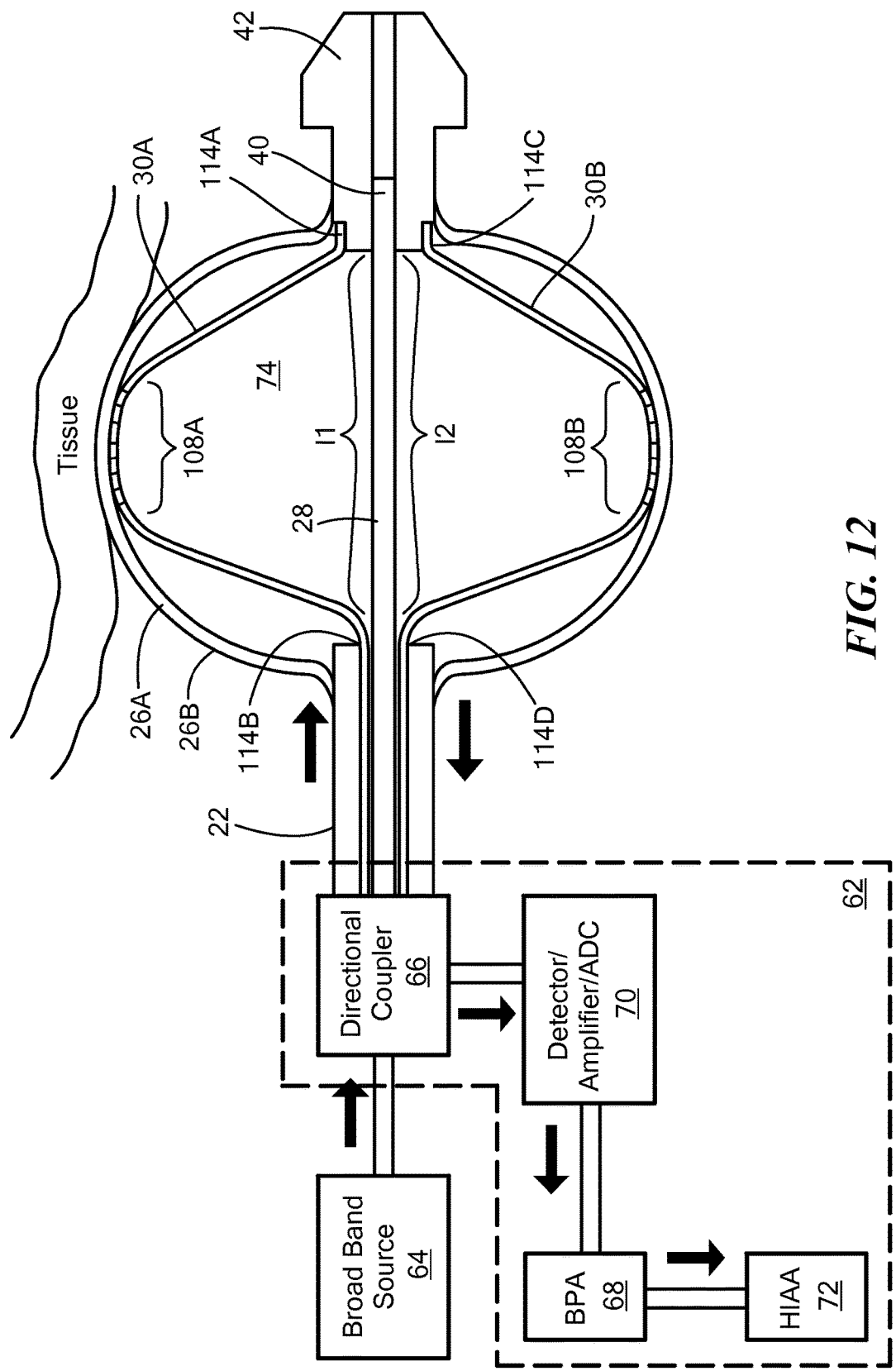
FIG. 12 shows an exemplary system including a cryotreatment device including a first fiber sensor and a second fiber sensor according to a fourth embodiment, the cryotreatment device positioned in direct contact with an area of tissue.
Figure 13:
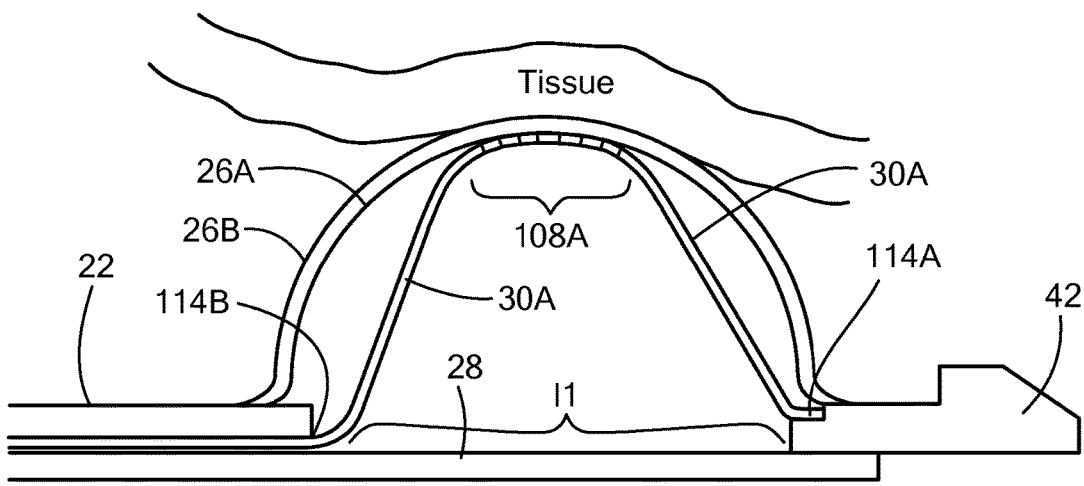
FIG. 13 shows a cross-sectional view of a portion of the cryotreatment device of FIG. 12, the cryotreatment device positioned in direct contact with an area of tissue.

The cryotreatment catheter 12 shown in FIGS. 12 and 13 may include a first fiber sensor 30A and a second fiber sensor 30B that are diametrically positioned within the inner chamber 74. The fiber sensors 30A, 30B may be SMF waveguides or may be as shown and described in FIG. 10, having a first 80A and a second 80B singlemode waveguide segments and a MMF waveguide segment 82. Further, the first 30A and second 30B fiber sensors may be coupled to the shaft 28 and the rotary mechanism 100 as described above. To overcome the sensitivity to temperature and strain, and indiscernibility between wavelength shifts associated with each, each fiber sensor 30A, 30B includes a portion with fiber Bragg grating (FBG) 108A, 108B, respectively, within the core 110 (although the fiber sensors 30A, 30B themselves are shown in FIGS. 12 and 13 as having the appearance of FBG on the outer surface for simplicity). The FBG may be created by a local refractive index modulation as a result of a photo-inscription by an ultraviolet (UV) illumination source. Light transmitted through the FBG may be affected by the grating. When a broadband signal is transmitted through the FBG, a wavelength $\lambda_B$ (referred to herein as the "Bragg's wavelength") may be filtered and reflected back while the other wavelengths are transmitted.

The Bragg's wavelength $\lambda_B$ may directly depend on the grating period $\Lambda$(nm) and the effective refractive index $n_{eff}$. As is shown in equation (1) below, the Bragg's wavelength is equal to two times the effective refractive index times the grating period:

$$\lambda B = 2n_{eff}\Lambda \qquad (1)$$

The shift in the wavelength ($\Delta\lambda_B$) with respect to the temperature and the axial strain change ($\Delta T$ and $\Delta\varepsilon$, respectively) may be represented according to equation (2) below:

$$\frac{\Delta\lambda B}{\lambda B} = (1 - \rho\epsilon)\Delta\epsilon + (\alpha + \xi)\Delta T \qquad (2)$$

where $\rho\epsilon$ is the photo-elastic coefficient of the fiber, $\alpha$ is the thermal expansion coefficient of the fiber material, and $\zeta$ is the thermo-optic coefficient of the fiber material.

Figure 14A:
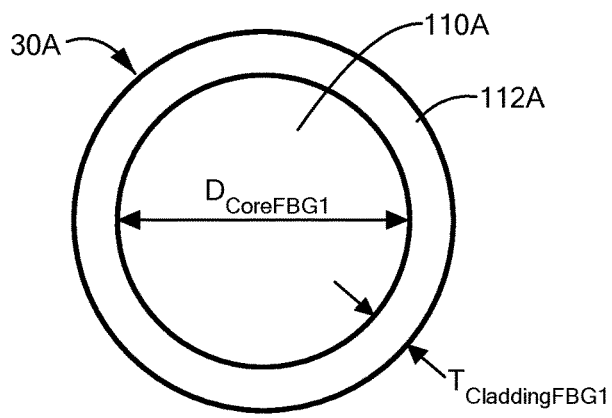
FIG. 14A shows a cross-sectional view of the first fiber sensor of the cryotreatment device of FIG. 12.
Figure 14B:
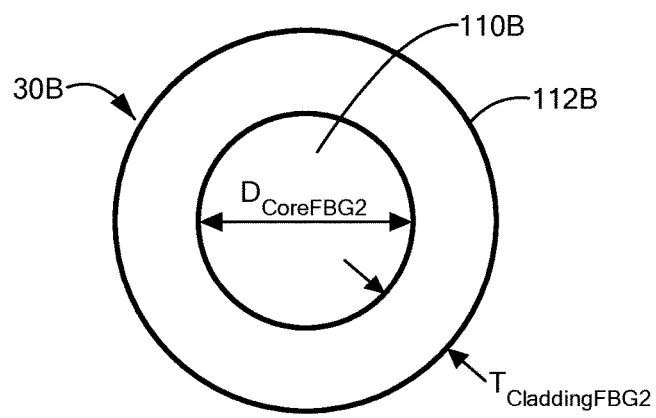
FIG. 14B shows a cross-sectional view of the second fiber sensor of the cryotreatment device of FIG. 12.

The fiber sensors 30A, 30B shown in FIGS. 12 and 13 may each include a core 110A, 110B and cladding 112A, 112B. The cores 110A, 110B of the FBGs 108A, 104B may have different diameters and the cladding 112A, 112E may have different thicknesses. For example, the FBG 108A of the first fiber sensor 30A may include a core 110A having a first diameter $D_{coreFBG1}$ and the FBG 108B of the second fiber sensor 30B may include a core 110B having a second diameter $D_{coreFBG2}$. As shown in FIGS. 14A and 14B, diameter $D_{coreFBG1}$ may be greater than diameter $D_{coreFBG2}$, and the thickness $T_{claddingFBG1}$ of fiber sensor 30A may be less than the thickness $T_{claddingFBG2}$ of fiber sensor 30B. However, it will be understood that diameter $D_{coreFBG2}$ may instead be greater than diameter $D_{coreFBG1}$ and thickness $T_{claddingFBG1}$ may be greater than $T_{claddingFBG2}$. Further, although the cross-sectional area of the sensors 30A, 30B may appear to be the same in the figures, it will be understood that the sensors 30A, 30B may have different cross-sectional areas. Using two fiber sensors with different cross-sectional area, Bragg's wavelengths, and/or lengths will lead to two distinct wavelength shifts. The relationship between wavelength shifts and the total strain experienced by the pair of FBGs 108A, 108B may be expressed in the following matrix:

$$\begin{pmatrix} \Delta\lambda B1 \\ \Delta\lambda B2 \end{pmatrix} = \begin{pmatrix} \frac{k\epsilon 1(l1 + l2)}{l1\left(1 + \frac{A_1 l_2}{A_2 l_1}\right)} & kT1 \\ \frac{k\epsilon 2(l1 + l2)}{l2\left(1 + \frac{A_2 l_2}{A_2 l_2}\right)} & kT2 \end{pmatrix} \begin{pmatrix} \Delta\varepsilon \\ \Delta T \end{pmatrix} \qquad (3)$$

where l1 and l2 are the lengths of the fiber sensor between the anchoring points 114A-114D at, for example, the shaft distal portion 40 (anchoring points 114A and 114C) and the location on each fiber 30A, 30B at which the fiber enters the elongate body 20 of the device 12 (anchoring points 114B and 114D). Although 114B and 114D may be referred to as an anchoring point, it will be understood that the fibers 30A, 30B are not actually coupled to the elongate body 20 and are instead free to move longitudinally, as discussed above. Further, although 114A and 114C may be referred to as anchoring "points," it will be understood that a length of the fiber sensors 30A, 30B, rather than only a single point, may be coupled or affixed to the shaft distal portion 40. A1 and A2 are the cross-sectional area of the fibers 30A, 30B, respectively, and k$\epsilon$ is a material parameter related to Poisson ratio (the negative ratio of transverse to axial strain). Finally, kT is related to the thermal expansion and thermo-optic coefficients of the fiber material.

The lengths l1 and l2 may be equal to enhance the simplicity and reliability of the rotary mechanism 100. The individual thermal and strain responses of the FBGs 108A, 108B may be determined separately. Therefore, the temperature and strain may be determined using the inverse of the matrix in equation (3). Depending on the force applied on the cryoballoon(s) 26 and the morphology of the tissue being treated, the fiber sensors 30A, 30B may have different lengths between the anchoring points 114A, 114C and anchoring points 114B, 114D. Additionally, if the cryotreatment catheter 12 is being used to perform a pulmonary vein isolation procedure, the quality of the occlusion of the pulmonary vein by the treatment element may also create a temperature difference between the FBGs 108A, 108B, which may result in a different shifting of the center wavelength for each FBG. However, the central wavelength spacing may be maintained.

In the embodiment shown in FIGS. 12 and 13, a light source 64 may be used. Light emitted by the light source 64 may be split equally between the first fiber sensor 30A and the second fiber sensor 30B, but the fiber sensors 30A, 30B may have different core diameters ($D_{coreFBG1}$ and $D_{coreFBG2}$) and different Bragg wavelengths ($\lambda$B1 and $\lambda$B2). As the light travels through the fiber sensors 30A, 30B, the portion of light that is equal to the Bragg wavelength of the corresponding fiber sensor 30 may be reflected by the corresponding FBG 104. The distal portions 94A, 94B of the fiber sensors 30A, 30B may be treated to prevent back reflection of the light toward the light source 64. Further, an isolator may be used to prevent reflected light from interfering with the light source 64. The directional coupler 66 may guide the reflected light toward the BPA 68, and BPA data may then be transmitted to the HIAA 72 for temperature and strain determination.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device comprising:
   an elongate body including a distal portion and a proximal portion;
   a shaft within the elongate body, the shaft including a distal portion;
   an inflatable treatment element at the distal portion of the elongate body, at least a portion of the inflatable element being coupled to the distal portion of the shaft, the inflatable treatment element defining an inner chamber; and
   at least one fiber sensor, at least a portion of each of the at least one fiber sensor being located within the inner chamber of the inflatable treatment element and including at least one singlemode waveguide segment and at least one multimode waveguide segment, each of the at least one fiber sensor including a proximal portion and a distal portion, the distal portion being coupled to the distal portion of the shaft and the proximal portion being freely movable within the inner chamber of the inflatable treatment element.

2. The device of claim 1, wherein the inflatable treatment element is a cryoballoon.

3. The device of claim 1, further including a handle coupled to the proximal portion of the elongate body, the handle including a rotary mechanism, the proximal portion of each of the at least one fiber sensor being engaged with the rotary mechanism.

4. The device of claim 1, wherein each of the at least one fiber sensor includes a first singlemode waveguide segment, a second singlemode waveguide segment, a third singlemode waveguide segment, a first multimode waveguide segment, and a second multimode waveguide segment.

5. The device of claim 4, wherein the first multimode waveguide segment is located between the first and second singlemode waveguide segments and the second multimode waveguide segment is located between the second and third singlemode waveguide segments.

6. The device of claim 5, wherein the inflatable treatment element includes an inner surface and the second singlemode waveguide is configured to be in contact with the inner surface when the inflatable treatment element is inflated.

7. The device of claim 6, wherein the inflatable treatment element further includes an outer surface and the outer surface of the inflatable treatment element is configured to be in contact with an area of target tissue when the inflatable element is inflated.

8. The device of claim 1, wherein each of the at least one fiber sensor includes a first singlemode waveguide segment, a second singlemode waveguide segment, and a multimode waveguide segment, the multimode waveguide segment being located between the first and second singlemode waveguide segments.

9. The device of claim 8, wherein the inflatable treatment element includes an inner surface and an outer surface, the multimode waveguide being configured to be in contact with the inner surface and the outer surface being configured to be in contact with an area of target tissue when the inflatable treatment element is inflated.

10. A medical system for determining a temperature of an area of tissue, the system comprising:
    a device including:
        an elongate body having a distal portion and a proximal portion;
        an inflatable treatment element at the distal portion of the elongate body, the inflatable treatment element including a grating;
        at least one fiber sensor, at least a portion of each of the at least one fiber sensor being located within the inflatable treatment element and including at least one singlemode waveguide segment and at least one multimode waveguide segment, at least a portion of the at least one fiber sensor being located proximate the grating; and
    a processing unit in communication with the at least one fiber sensor, the processing unit including:
        a beam processing apparatus configured to receive light transmitted through the at least one fiber sensor; and
        a hyperspectral imaging and analysis apparatus configured to calculate a temperature of the area of tissue.

11. The system of claim 10, wherein each of the at least one fiber sensor includes a first singlemode waveguide segment, a second singlemode waveguide segment, a third singlemode waveguide segment, a first multimode waveguide segment, and a second multimode waveguide segment.

12. The system of claim 11, wherein the first multimode waveguide segment is located between the first and second singlemode waveguide segments and the second multimode waveguide segment is located between the second and third singlemode waveguide segments.

13. The system of claim 12, wherein the inflatable treatment element includes an inner surface and an outer surface, the second singlemode waveguide being configured to be in contact with the inner surface proximate the grating and the outer surface being configured to be in contact with the area of tissue when the inflatable treatment element is inflated.

14. The system of claim 10, wherein each of the at least one fiber sensor includes a first singlemode waveguide segment, a second singlemode waveguide segment, and a multimode waveguide segment, the multimode waveguide segment being located between the first and second singlemode waveguide segments.

15. The system of claim 14, wherein the inflatable treatment element includes an inner surface and an outer surface, the multimode waveguide being configured to be in contact with the inner surface proximate the grating and the outer surface being configured to be in contact with an area of target tissue when the inflatable treatment element is inflated.

16. The system of claim 10, further comprising a light source configured to transmit light to the at least one fiber sensor.

* * * * *